United States Patent [19]

Schiehser et al.

[11] Patent Number: 4,587,345

[45] Date of Patent: May 6, 1986

[54] PROCESS FOR PREPARING THIENO-FUSED HETEROCYCLIC ANTI-ULCER AGENTS

[75] Inventors: Guy A. Schiehser, Malvern; Donald P. Strike, St. Davids, both of Pa.

[73] Assignee: American Home Products Corporation, New York, N.Y.

[21] Appl. No.: 655,978

[22] Filed: Sep. 28, 1984

[51] Int. Cl.[4] .................. C07D 513/04; C07D 333/34
[52] U.S. Cl. .................................. 548/212; 548/210; 549/60
[58] Field of Search .................. 548/212, 210, 211

[56] References Cited

U.S. PATENT DOCUMENTS

| | | | |
|---|---|---|---|
| 4,028,373 | 6/1977 | Hromatka et al. | 548/210 |
| 4,104,388 | 8/1978 | Wade et al. | 548/210 |
| 4,490,527 | 12/1984 | Schiehser et al. | 548/212 |

OTHER PUBLICATIONS

Rossy et al., "Aromatization of Dihydrothiophenes . . . ," *J. Org. Chem.*, 45: pp. 617–620 (1980).
Imai et al., "Ring–Opening Polymerization of Ethansultam," *Chem. Abst.*, 82:98451(p) (1974).

*Primary Examiner*—Mark L. Berch
*Assistant Examiner*—G. Hendricks
*Attorney, Agent, or Firm*—George Tarnowski

[57] ABSTRACT

A process for preparing certain thieno-fused heterocyclic compounds having $H_2$-receptor antagonist and antisecretory activity, which comprises reacting a suitable thienoisothiazole derivative with an appropriate (furanylmethylthio)ethanamine derivative to yield an intermediate, which is subjected to cyclization to yield the desired final product.

2 Claims, No Drawings

PROCESS FOR PREPARING THIENO-FUSED HETEROCYCLIC ANTI-ULCER AGENTS

This invention relates to a novel process for the preparation of certain thieno-fused heterocyclic compounds. Some of these compounds are disclosed in pending U.S. Ser. No. 468,221, now U.S. Pat. No. 4,490,527 filed Feb. 22, 1983, by Guy A. Schiehser and Donald P. Strike. The process of the present invention gives the products in good overall yield from conveniently available starting materials.

The present invention provides a process for the preparation of thieno-fused heterocyclic compounds of the formula

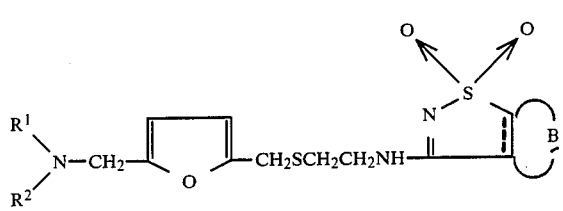

wherein
B is a moiety having the formula

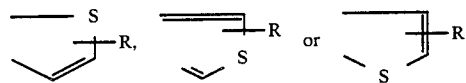

R is hydrogen, mono- or dihalo, nitro, cyano, trifluoromethyl, mercapto, lower alkyl, lower alkoxy, alkanoyl, lowercycloalkyl, carboxy, alkoxycarbonyl, mono- or di-lower alkyl substituted amino, alkanoylamino, lower alkyl thio, loweralkylsulfonyl, lower alkyl substituted sulfamoyl, phenyl or phenyl substituted with halo, lower alkyl, lower alkoxy, trifluoromethyl, cyano or nitro;

$R^1$ and $R^2$ are each lower alkyl or $R^1$ and $R^2$ taken together, optionally with a hetero atom, form a saturated 5- or 6-membered heterocyclic ring;
and the pharmacologically acceptable salts thereof, which comprises (A) reacting a suitable thienoisothiazole derivative of the formula

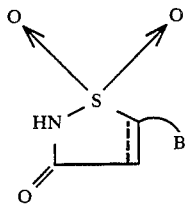

with an amine having the formula

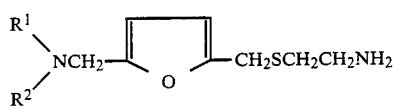

wherein B, $R^1$ and $R^2$ are as defined hereinbefore, and treating the reaction mixture with oxalic acid to form the following intermediate

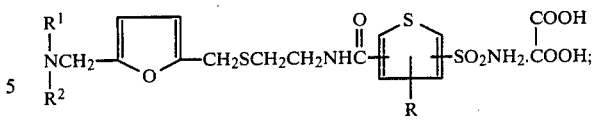

and (B) cyclizing the intermediate obtained in Step A in the presence of a cyclizing agent to yield a compound having the formula

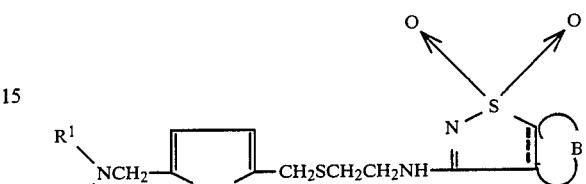

wherein B, $R^1$ and $R^2$ are as defined hereinbefore, and if desired, converting a resulting free base into a pharmacologically acceptable salt.

The term "halo" refers to fluoro, chloro and bromo. The terms "loweralkyl" and "loweralkoxy" refer to moieties having 1 to 6 carbon atoms in the carbon chain. The term "lower cycloalkyl" refers to cyclic structures having 5 to 7 carbon atoms. The term "alkanoyl" refers to the moiety RCO— wherein R is an alkyl group having 1 to 4 carbon atoms. In the case where the substituents $R^1$ and $R^2$ are taken together, optionally with a heteroatom, to form a 5- or 6-membered saturated heterocyclic ring, the cyclic secondary amines so formed include, among others, pyrrolidinyl, imidazolidinyl, pyrazolidinyl, piperazinyl, piperidino, morpholino, thiomorpholino and the like.

The reaction of Step A above is carried out at elevated temperature under a nitrogen atmosphere. The reaction mixture is subjected to preparative chromatography to recover the desired reaction product, which is then treated with oxalic acid to obtain the mono-oxalate salt. This mono-oxalate salt of the intermediate is then purified by recrystallization procedures conventional in the art.

In Step B of the process, the mono-oxalate salt of the intermediate of Step A is subjected to cyclization in the presence of a cyclizing agent, preferably phosphorous oxychloride. This step is carried out at an elevated temperature. The desired final product is recovered by column chromatography and purified by procedures conventional in the art.

The final products obtained in their free base form can be converted into pharmacologically acceptable salts by standard procedures. For example, the free base can be dissolved in a suitable organic solvent and the solution treated with a solution of the selected acid, in accordance with conventional procedures for preparing pharmacologically acceptable salts. As examples of suitable acids, there may be used hydrochloric, hydrobromic, sulfuric, nitric, phosphoric, acetic, maleic, fumaric, citric, methanesulfonic, p-toluenesulfonic and the like.

The starting compound thienoisothiazole derivatives can be prepared from available compounds or are commercially available.

The thienoisothiazole derivatives having the formula

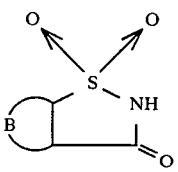

where B is as hereinbefore defined, can be prepared according to the following reaction scheme, as described by Rossy et al., *J. Org. Chem.*, 45, 617 (1980):

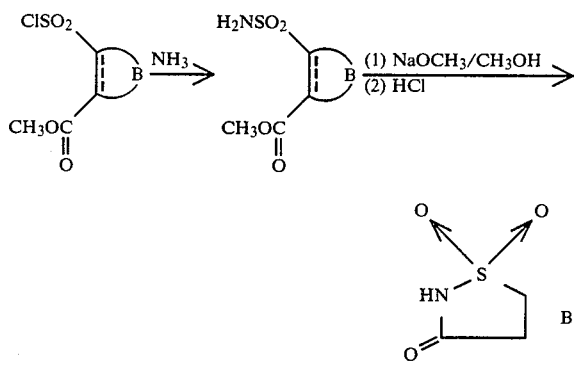

The starting intermediates having the formula

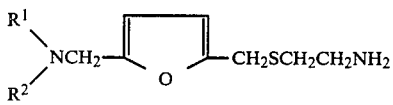

can be conveniently prepared according to the following procedure described in U.S. Pat. No. 4,128,658, as for example the dimethylaminomethyl derivative:

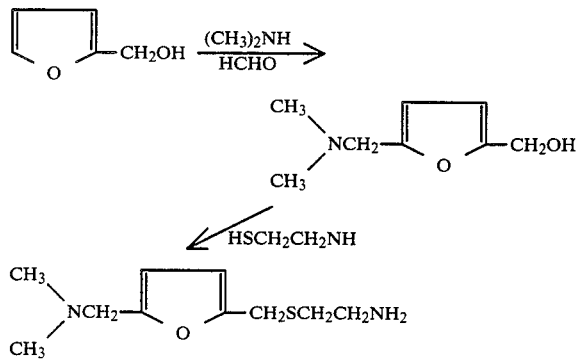

The resulting desired intermediate can be recovered by known means and can be used directly in the process of the invention.

The process of the invention can be used to prepare compounds such as those disclosed in U.S. Ser. No. 468,221 now U.S. Pat. No. 4,490,527 and which have been described, supra. These compounds are potent $H_2$-receptor antagonists and antisecretory agents, which are useful in the treatment of conditions where there is hypersecretion of gastric acid, such as in gastric and peptic ulceration, and other conditions caused or exacerbated by gastric acidity, such as stress ulceration or gastric intestinal bleeding due to trauma.

The following examples illustrate this invention.

Preparation of
2-[[[5-(Dimethylamino)methyl-2-furanyl]methyl]thio]ethanamine (1) 5-(Dimethylamino)methyl-2-furanmethanol A mixture of 196 g (2 mol) of furfuryl alcohol, 245 g (3 mol) of dimethylamine hydrochloride and 200 mL of 37% formaldehyde is stirred at 0° C. for 3 hours. The mixture is allowed to warm to room temperature and is stirred for 20 hours.

The mixture is treated with 750 g of sodium carbonate and the resulting slurry is extracted sequentially with ethyl acetate and acetone. The combined organic extracts are rotoevaporated and distilled to give, in two fractions, 209 g (67.3 %) of the title compound.

Fraction A:

b.p. 91°–96° C. [0.4 mm] 147.1 g.

Analysis for: $C_8H_{13}NO_2$, Calculated: C, 61.91; H, 8.44; N, 9.03, Found: C, 61.25; H, 8.59; N, 8.86.

Fraction B:

b.p. 96°–98° C. [0.4 mm] 61.9 g.

Analysis for: $C_8H_{13}NO_2$, Calculated: C, 61.91; H, 8.44; N, 9.03, Found: C, 61.79; H, 8.41; N, 9.19.

(2)
2-[[[5-(Dimethylamino)methyl-2-furanyl]methyl]thio]ethanamine

To a solution of 89.5 g (0.79 mol) of aminoethanethiol hydrochloride in 300 mL of concentrated hydrochloric acid maintained between −10 and 0° C. is added dropwise over 75 minutes, 116.4 g (0.75 mol) of 5-(dimethylamino)methyl-2-furanmethanol.

The mixture is placed under refrigeration (5° C.) for 63 hours and then treated portionwise with 825 g of anhydrous sodium carbonate. The resulting slurry is exhaustively extracted with ethyl acetate and the organic extract dried over magnesium sulfate and rotoevaporated. Distillation of the crude product gives, in two fractions, a total of 62.7 g (26.6%) of the title compound.

Fraction A:

b.p. 122° C. [0.5 mm] 34.4 g.

Analysis for: $C_{10}H_{18}N_2OS$, Calculated: C, 56.04; H, 8.46; N, 13.07, Found: C, 55.66; H, 8.42; N, 12.92.

Fraction B:

b.p. 123° C. [0.5 mm] 28.3 g.

Analysis for: $C_{10}H_{18}N_2OS$, Calculated: C, 56.04; H, 8.46; N, 13.07, Found: C, 55.76; H, 8.29, H, 12.99.

EXAMPLE 1

N-[2-[[[5-[(Dimethylamino)methyl]-2-furanyl]methyl]thio]ethyl]thieno[3,4-d]isothiazol-3-amine 1,1-dioxide (A) 4-Aminosulfonyl-N-[2-[[[5-[(dimethylamino)methyl]-2-furanyl]methyl]thio]ethyl]-3-thiophene-carboxyamide, ethanedioate.

A mixture of 2.14 g (10 mmol) of 2-[[[5-[(dimethylamino)methyl]-2-furanyl]methyl]thio]ethanamine and 1.89 g (10 mmol) of thiophene saccharin[1] is heated to 160° C. under a nitrogen atmosphere and maintained for 30 minutes.

[1] Prepared according to the procedure described by Rossy et al., *J. Org. Chem.*, 45, 617 (1980).

The crude product is chromatographed preparatively on silica gel utilizing methylene chloride:methanol:ammonium hydroxide (95:5:0.5) as eluting solvent. The appropriate fractions are combined and rotoevaporated to give 2.4 g of an oily foam. Treatment with ethanolic oxalic acid affords a crude mono-oxalate salt which gives, upon recrystallization from ethanol, 889 mg of the title compound: m.p. 120°–124° C.

Analysis for: $C_{15}H_{21}N_3O_4S_3 \cdot C_2H_2O_4$, Calculated: C, 41.34; H, 4.70; N, 8.51, Found: C, 41.74; H, 4.72; N, 8.54.

(B)

N-[2-[[[5-[(dimethylamino)methyl]-2-furanyl]methyl]thio]ethyl]thieno[3,4-d]isothiazol-3-amine, 1,1-dioxide A mixture of 462 mg (1 mmol) of 4-(aminosulfonyl)-N-[2-[[[5-[(dimethylamino)methyl]-2-furanyl]methyl]thio]ethyl]-3-thiophene-carboxamide, ethaneodioate in 25 ml of phosphorus oxychloride is heated to 110° C. and maintained for 45 minutes.

Rotoevaporation gives an oil which is subjected to column chromatography on silica gel utilizing methylene chloride:methanol:ammonium hydroxide (95:5:0.5) as eluting solvent. The appropriate fractions are combined, rotoevaporated and treated with ethanolic hydrochloric acid. Evaporation followed by trituration with acetonitrile gives 39 mg of the title compound: m.p. 179°–186° C.

Analysis for: $C_{15}H_{19}N_3O_3S_3 \cdot HCl$, Calculated: C, 42.69; H, 4.78; N, 9.96, Found: C, 42.34; H, 4.83; N, 9.77.

What is claimed is:

1. A process for the preparation of compounds of the formula

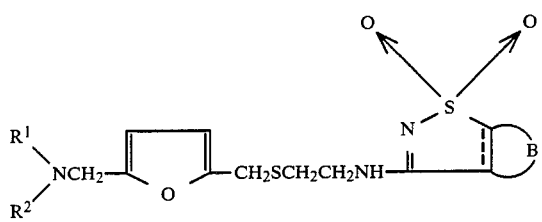

wherein

B is a moiety having the formula

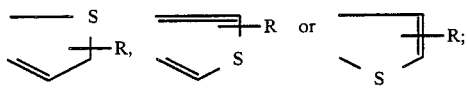

R is hydrogen, mono- or dihalo, nitro, cyano, trifluoromethyl, mercapto, lower alkyl, lower alkoxy, alkanoyl, lowercycloalkyl, carboxy, alkoxycarbonyl, mono- or di-lower alkyl substituted amino, alkanoylamino, lower alkyl thio, loweralkylsulfonyl, lower alkyl substituted sulfamoyl, phenyl or phenyl substituted with halo, lower alkyl, lower alkoxy, trifluoromethyl, cyano or nitro;

$R^1$ and $R^2$ are each lower alkyl and the pharmacologically acceptable salts thereof, which comprises (A) reacting a suitable thienoisothiazole of the formula

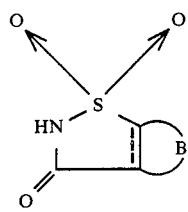

with an amine having the formula

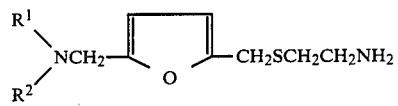

wherein B, $R^1$ and $R^2$ are as defined hereinbefore, and treating the reaction mixture with oxalic acid to form the following intermediate

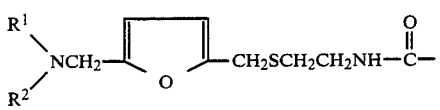

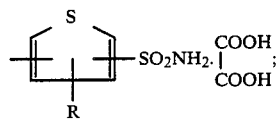

and (B) cyclizing the intermediate obtained in Step A in the presence of a cyclizing agent to yield a compound having the formula

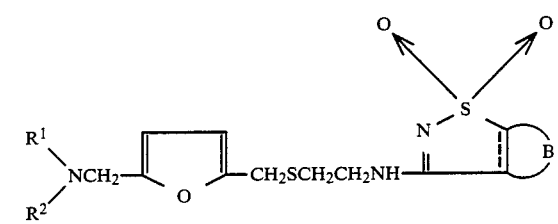

wherein B, $R^1$ and $R^2$ are as defined hereinbefore, and if desired, converting a resulting free base into a pharmacologically acceptable salt.

2. The process of claim 1, wherein the compound prepared is N-[2-[[[5-[(dimethylamino)methyl]-2-furanyl]methyl]thio]ethyl]thieno[3,4-d]isothiazol-3-amine 1,1-dioxide.

* * * * *